United States Patent
Goto et al.

(10) Patent No.: US 9,380,929 B2
(45) Date of Patent: Jul. 5, 2016

(54) ENDOSCOPE WITH AN OPTICAL MEMBER, A FRAME PORTION AND A BONDING MEMBER SOLDERING THE OPTICAL MEMBER TO THE FRAME PORTION

(71) Applicant: OLYMPUS CORPORATION, Tokyo (JP)

(72) Inventors: Atsushi Goto, Tokyo (JP); Hiroaki Kinoshita, Tokyo (JP)

(73) Assignee: Olympus Corporation, Tokyo (JP)

( * ) Notice: Subject to any disclaimer, the term of this patent is extended or adjusted under 35 U.S.C. 154(b) by 37 days.

(21) Appl. No.: 14/257,536

(22) Filed: Apr. 21, 2014

(65) Prior Publication Data

US 2014/0275786 A1  Sep. 18, 2014

Related U.S. Application Data

(63) Continuation of application No. PCT/JP2013/077756, filed on Oct. 11, 2013.

(30) Foreign Application Priority Data

Oct. 12, 2012  (JP) .................................. 2012-227265

(51) Int. Cl.
*A61B 1/06* (2006.01)
*A61B 1/04* (2006.01)
(Continued)

(52) U.S. Cl.
CPC ........... *A61B 1/00071* (2013.01); *A61B 1/0011* (2013.01); *A61B 1/00096* (2013.01); *A61B 1/00142* (2013.01); *G02B 23/243* (2013.01); *G02B 23/2476* (2013.01); *G02B 23/26* (2013.01)

(58) Field of Classification Search
CPC ............. A61B 1/00064; A61B 1/0011; A61B 1/00071; A61B 1/0008; A61B 1/00096; A61B 1/00142; A61B 1/05
USPC ......... 600/109, 129, 133, 160, 172, 175, 176, 600/177
See application file for complete search history.

(56) References Cited

U.S. PATENT DOCUMENTS 4,872,740 A * 10/1989 Terada .................... G02B 23/26
385/117
5,258,441 A * 11/1993 Nagahiro ................ C08L 79/08
524/425
(Continued)

FOREIGN PATENT DOCUMENTS

CN  1 495 020  5/2004
EP  0 304 118  2/1989
(Continued)

OTHER PUBLICATIONS

International Search Report (in Japanese), issued in corresponding International Application No. PCT/JP2013/077756.
(Continued)

*Primary Examiner* — John P Leubecker
*Assistant Examiner* — William Chou
(74) *Attorney, Agent, or Firm* — Kenyon & Kenyon LLP

(57) ABSTRACT

An endoscope includes a lens, a lens frame that holds the lens, and a bonding member that water-tightly fixes the lens to the lens frame, the bonding member composed of Sn-alloy solder containing at least one of Zn, Sb, Al and In, having a melting point not higher than 200° C. and forming a chemical bond via oxygen, and the lens, the lens frame and the bonding member are provided at a distal end portion of an insertion portion.

9 Claims, 3 Drawing Sheets

(51) Int. Cl.
  *A61B 1/00* (2006.01)
  *G02B 23/26* (2006.01)
  *G02B 23/24* (2006.01)

(56) References Cited

U.S. PATENT DOCUMENTS

| | | | |
|---|---|---|---|
| 6,547,721 | B1 | 4/2003 | Higuma et al. |
| 2001/0040290 | A1* | 11/2001 | Sakurai ............... H01L 23/3128 257/737 |
| 2004/0248059 | A1 | 12/2004 | Katsuda et al. |

FOREIGN PATENT DOCUMENTS

| | | |
|---|---|---|
| EP | 0978251 | 2/2000 |
| GB | 2 215 087 | 9/1989 |
| JP | 61-144613 | 7/1986 |
| JP | 08-271807 | 10/1996 |
| JP | 2000-139821 | 5/2000 |
| JP | 2002-253487 | 9/2002 |
| JP | 2002-325728 | 11/2002 |
| JP | 2003-175001 | 6/2003 |
| JP | 2003-180621 | 7/2003 |
| JP | 2003-204934 | 7/2003 |
| JP | 2004-082199 | 3/2004 |
| JP | 2004-355852 | 12/2004 |
| JP | 2006-223763 | 8/2006 |
| JP | 2012-006054 | 1/2012 |

OTHER PUBLICATIONS

Supplementary European Search Report, dated Sep. 22, 2015, issued in corresponding European Patent Application No. 13845135.6.

* cited by examiner

ENDOSCOPE WITH AN OPTICAL MEMBER, A FRAME PORTION AND A BONDING MEMBER SOLDERING THE OPTICAL MEMBER TO THE FRAME PORTION

CROSS REFERENCE TO RELATED APPLICATION

This application is a continuation application of PCT/JP2013/077756 filed on Oct. 11, 2013 and claims benefit of Japanese Application No. 2012-227265 filed in Japan on Oct. 12, 2012, the entire contents of which are incorporated herein by this reference.

BACKGROUND OF THE INVENTION

1. Field of the Invention

The present invention relates to an endoscope in which an optical member is water-tightly fixed to a distal end portion of an insertion portion.

2. Description of the Related Art

An endoscope for observing inside of a body of a subject by an image pickup section disposed at a distal end portion and performing remedy/treatment using a treatment instrument projected from the distal end portion by inserting an elongated insertion portion into the body of the subject which cannot be observed from outside is widely used. The endoscope after use is disinfected and sterilized in order to prevent inter-patient infection via the endoscope.

As a disinfecting and sterilization method for an endoscope, an autoclave method (high-temperature and high-pressure steam method) becomes mainstream. In the autoclave method, any complicated operation is not required and the endoscope can be used immediately after sterilization and a running cost is low. However, in the autoclave method, since an entire endoscope is subjected to a high-temperature and high-pressure state, an O-ring or the like that water-tightly seals a lens of an image pickup optical system or the like disposed at the distal end portion and a lens frame for holding the lens, tends to deteriorate so that there is a fear that steam invades the optical system. Similarly, if the lens is fixed to the lens frame with adhesive composed of resin, there is a case where the steam invades a space inside the lens frame and the lens is fogged from inside.

In Japanese Patent Laid-Open Publication No. 2002-253487, an endoscope in which a lens is fixed to a lens frame by solder is disclosed. The above endoscope realizes water-tight seal with high reliability by using solder, which is a metal material, as a bonding member.

In Japanese Patent Laid-Open Publication No. 2004-82199, there is disclosed solder that can be bonded to an optical member composed of an oxide such as glass. By using the solder disclosed in the above publication, the lens can be fixed to the lens frame without forming a metal film for soldering on the lens.

SUMMARY OF THE INVENTION

An endoscope according to an embodiment includes: an optical member having a solder-repellant layer applied on an outer circumferential portion of an outer surface in a doughnut shape, with a ridge line on which a distal end surface and a side surface of the optical member intersect being chamfered, the solder-repellant layer composed of magnesium fluoride, aluminum nitride, boron nitride, silicon nitride, silicon carbide, boron carbide, calcium carbide, diamond-like carbon, polytetrafluoroethylene or rafluoroethylene-perfluoro alkyl vinyl ether copolymer; a black layer containing carbon and applied on a side surface of the optical member; a frame portion that holds the optical member; and a bonding member that water-tightly fixes the optical member to the frame portion and covers the side surface and a chamfered surface of the optical member, the bonding member composed of lead-free Sn-alloy solder containing at least one of Zn, Sb, Al and In, having a melting point not higher than 200° C. and forming a chemical bond via oxygen, wherein the optical member, the black layer, the frame portion and the bonding member are provided at a distal end portion of an insertion portion.

An endoscope according to another embodiment includes: an optical member having a solder-repellant layer applied on an outer circumferential portion of an outer surface in a doughnut shape, the solder-repellant layer composed of metal carbide, metal nitride, metal boride, metal fluoride, fluororesin or carbon material; a frame portion that holds the optical member; and a bonding member that water-tightly fixes the optical member to the frame portion, the bonding member composed of Sn-alloy solder containing at least one of Zn, Sb, Al and In, having a melting point not higher than 200° C. and forming a chemical bond via oxygen, wherein the optical member, the frame portion and the bonding member are provided at a distal end portion of an insertion portion.

DETAILED DESCRIPTION OF THE PREFERRED EMBODIMENTS

First Embodiment

Figure 1:
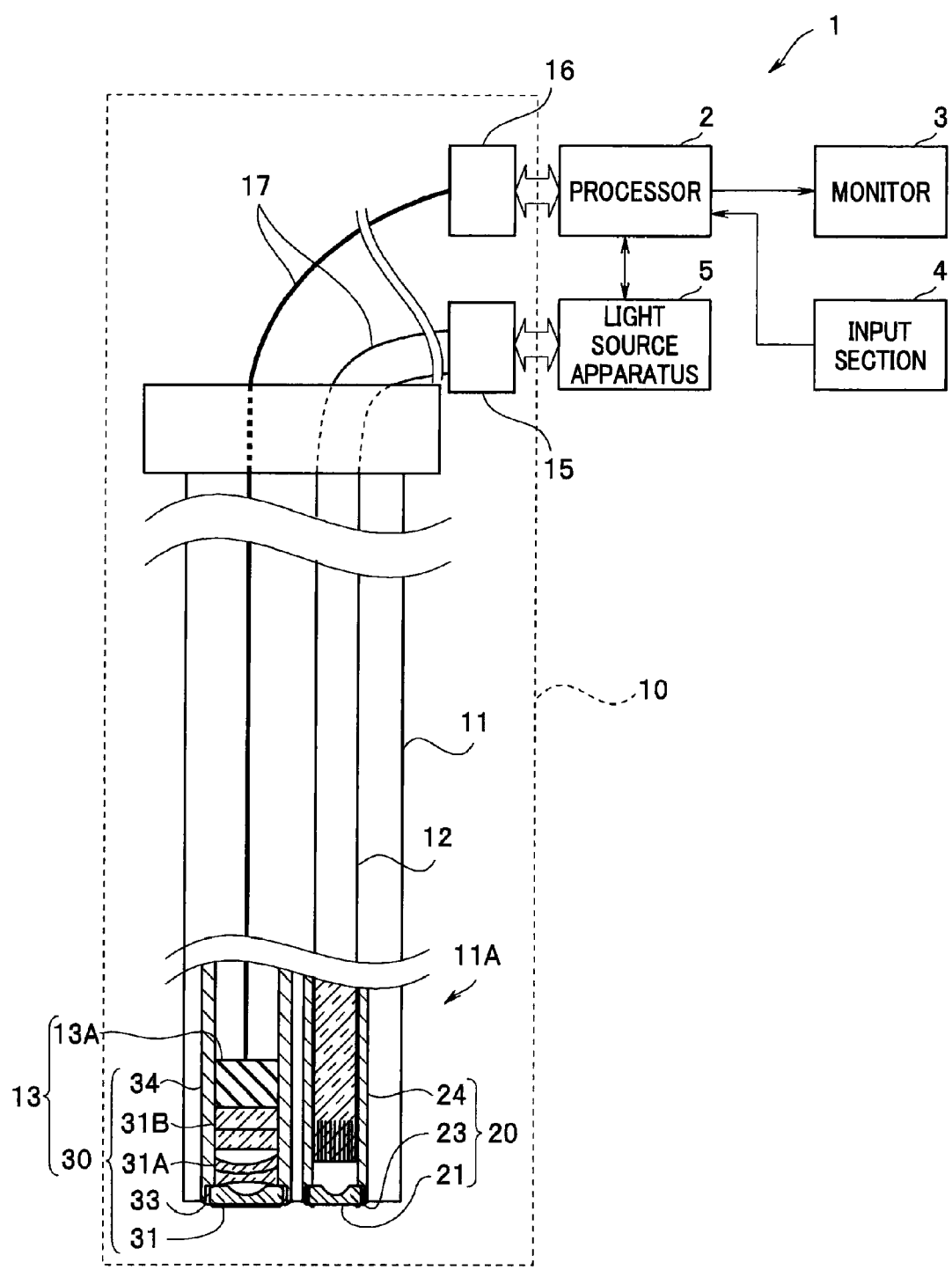
FIG. 1 is a configuration diagram of an endoscope system including an endoscope according to an embodiment.

As shown in FIG. 1, an endoscope 10 of the present embodiment constitutes an endoscope system 1 with a processor 2 that processes image signals, a monitor 3, an input section 4 for setting conditions of use, etc. and a light source apparatus 5.

The endoscope 10 includes an elongated insertion portion 11 to be inserted into a body, a universal cord 17 extended from the insertion portion 11 through an operation portion (not shown). The insertion portion 11 through which a light guide 12 is inserted includes an image pickup section 13 in a distal end portion 11A. The image pickup section 13 includes an image pickup optical unit 30 (hereinafter referred to as "optical unit 30") and an image pickup device 13A such as a CCD. The universal cord 17 includes, on a proximal end side, a light guide connector 15 connected with the light source apparatus 5 and an electronic connector 16 connected with the processor 2.

Light generated by the light source apparatus 5 is guided to the distal end portion 11A through the light guide connector 15 and the light guide 12, and emitted toward a subject as illumination light through an irradiation optical unit 20 (hereinafter referred to as "optical unit 20"). The illumination light reflects on a surface of the subject and reflected light is picked up as a subject image by the image pickup device 13A through the optical unit 30. The image is subjected to signal processing by the processor 2 and displayed on a screen of the monitor 3.

On a distal end face, for example, of the distal end portion 11A, a circular lens 21 which is an optical member of the optical unit 20, and a circular lens 31 which is an optical member of the optical unit 30 are disposed.

Figure 2:
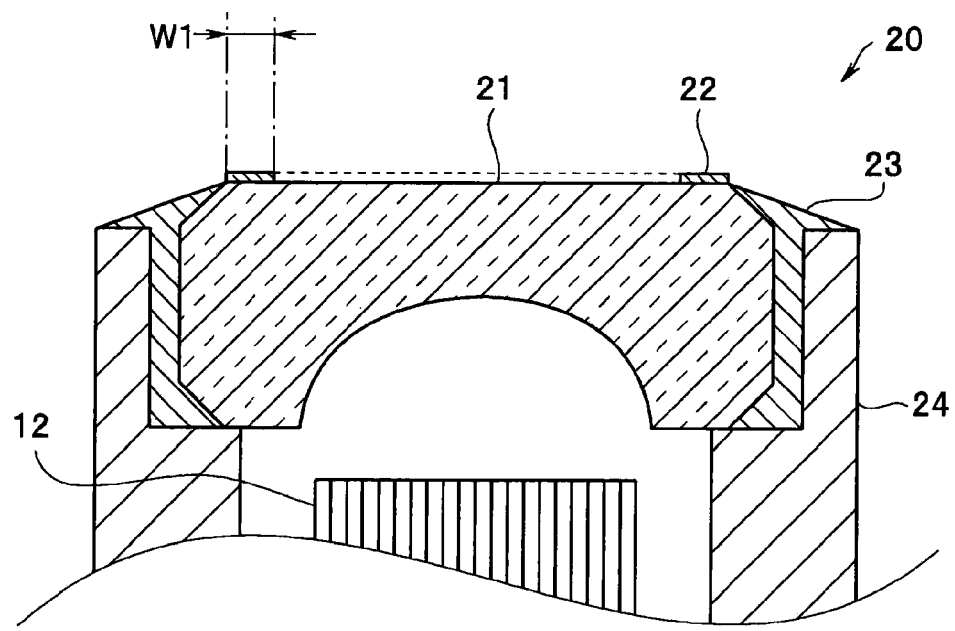
FIG. 2 is a sectional view of an irradiation optical unit of an endoscope according to a first embodiment.

As shown in FIGS. 1 and 2, the optical unit 20 includes the lens 21, a lens frame 24 as a frame portion which holds the lens 21, a bonding member 23 which is composed of solder and water-tightly fixes the lens 21 to the lens frame 24. On the other hand, the optical unit 30 includes the lens 31, lenses 31A and 31B, a lens frame 34 as a frame portion which holds the lenses 31, etc., a bonding member 33 which is composed of solder and water-tightly fixes the lens 31 to the lens frame 34.

Besides, in the endoscope 10, the lens frame 24 of the optical unit 20 and the lens frame 34 of the optical unit 30 are separated, but the lens 21 and the lens 31 may be fixed to a common lens frame. Further, peripheral regions of the lens 21 and the lens 31 at the distal end portion 11A may be covered by resin.

The lenses 21 and 31 are made of an optical material such as quartz or sapphire. Other than these materials, transparent optical materials such as stabilized zirconia (YSZ), yttrium aluminum garnet (YAG) can be used. Further, amorphous glass having a high tolerance against the autoclave, e.g. the glass described in U.S. Pat. No. 6,558,316 can be used.

As described later, the solder of the bonding members 23 and 33 is composed of Sn alloy which contains at least one of Zn, Sb, Al and In and has a melting point not higher than 200° C. The lens frames 24 and 34 are made of metal, e.g. stainless steel. Further, at an outer circumferential portion of an outer surface of the lens 21, a solder-repellant layer 22 is formed into a film in a doughnut shape. The solder-repellant layer 22 is composed of PTFE (polytetrafluoroethylene), for example.

The solder of the bonding member 23 has high solder wettability with a material containing oxygen. For example, the solder is leadless solder (lead-free solder) which has composition of Sn, as a principal component, with Zn, Sb and Al added. Zn improves bondability, Sb improves weather resistance and moisture resistance, and Al prevents rapid oxidization of the solder. That is, it is particularly preferable that the solder of the bonding members 23 and 33 be composed of Sn alloy containing Zn, Sb and Al. It is noted that a melting temperature can be adjusted by adding In in addition. It is noted that flux is not used in bonding.

For example, an addition amount of Sb may be of a degree of being contained in the principal component of Sn as an impurity, and an addition amount of Zn is 1.0 wt % to 7.5 wt %, an addition amount of Al is 0.02 wt % to 0.1 wt %, an addition amount of In is 0 wt % to 5 wt %.

Further, if it is unnecessary that the solder is the lead-free solder, the composition may be such that Zn, Sb, Al, Ti, Si or Cu and the like are added to Pb—Sn alloy.

Since the solder having the above composition forms a chemical bond with a material containing oxygen via the oxygen, the water-tight seal in which bonding strength is high and the weather resistance and the moisture resistance are high is enabled.

The solder of the bonding members 23 and 33 has high solder wettability with an oxide and can bond the lenses 21 and 31 composed of the material containing oxygen to the lens frame 24 and 34, respectively, without any other member intervened. That is, it is not necessary to form a metal film for solder bonding on an entire circumference of a side surface of the lens as required in a conventional endoscope. Therefore, the endoscope 10 is easily manufactured.

Besides, so-called low-temperature solder, which has a melting point not higher than 200° C., preferably not higher than 150° C., e.g. 130° C., is used as the bonding member 23. If high-temperature solder is used, there is a case where the lens is broken to bring a low yield rate that causes an increase in cost. However, by using the low-temperature solder, since the temperature in bonding is low, there is not any fear that the lenses 21 and 31 are damaged.

It is noted that a lower limit of the melting point of the solder of the bonding member 23 is 110° C., for example.

Here, the soldering by the solder of the bonding members 23 and 33 is performed while applying ultrasound vibration so as to remove bubbles intervened between a bonding object and melted solder. Therefore, there has been a fear that the melted solder overflows from the side surface of the lens to the outer surface of the lens.

It is preferable that the ultrasound vibration applied in a state of heating at 100° C.-200° C. has a frequency of 5 kHz to 200 kHz and a power of 5 W to 200 W. The ultrasound may be applied directly to the solder or from an outer circumference of the lens frame 24. That is, the ultrasound vibration is transmitted from the outer circumference to an inner circumference of the lens frame 24. The effect of the ultrasound vibration becomes the maximum at a position where cavitation is generated. Therefore, adherence on the entire bonding surfaces can be improved by changing the position where the cavitation is generated by changing the frequency or the power or the like.

It is noted that very high workability can be obtained by heating the solder in a ring shape matched with an outer diameter of the lens (an inner diameter of the lens frame) in a state where the solder is arranged between the lens and the lens frame. Besides, it is preferable that the outer diameter of the ring solder is greater than the outer diameter of the lens by 1 μm to 30 μm.

In the endoscope 10, the solder-repellant layer 22 made of PTFE is formed into a film in a doughnut shape on the outer circumferential portion of the lens 21. PTFE is a solder-repellant material which has low solder wettability to "shed the solder" as it is called. PTFE has heat resistance temperature higher than solder bonding temperature.

It is noted that the solder wettability can be evaluated by melting 20 mg solder on a test surface and measuring a contact angle θ of the melted solder with respect to the test surface. The contact angle θ of the solder of the bonding member 23 with respect to the optical member such as quartz or sapphire is less than 30 degrees, whereas the contact angle θ with respect to PTFE is not less than 70 degrees.

As the solder-repellant layer 22, a material with which the contact angle θ of the solder is not less than 45 degrees, preferably not less than 60 degrees can be used from among solder-repellant materials not containing oxygen. The solder-repellant layer 22 with which the contact angle θ of the solder is not less than the above range can prevent the melted solder from spreading on the outer surface of the lens. It is preferable that the contact angle θ is greater and an upper limit thereof may be 180 degrees.

Besides, instead of the measurement of the contact angle, the bonding strength may be measured as a simple measuring method. That is, the solder bonded with the solder-repellant material having low solder wettability has low bonding strength. For example, adhesive strength of the solder bonded with the solder-repellant material with which the contact angle θ of the solder is not less than 60 degrees is not greater than 1 MPa. By contrast, adhesive strength of the solder bonded with the solder-repellant material with which the contact angle θ of the solder is less than 30 degrees is not less than 10 MPa, e.g. 20 MPa.

Besides, although the solder bonding is actually performed while applying the ultrasound vibration, it is preferable that the solder bonding is performed without applying the ultrasound vibration when measuring the contact angle, etc. This is because the solder easily spread by the ultrasound vibration.

As the solder-repellant material, more specifically, magnesium fluoride, aluminum nitride, boron nitride, silicon nitride, silicon carbide, boron carbide, calcium carbide, diamond-like carbon (DLC), polytetrafluoroethylene (PTFE) or tetrafluoroethylene-perfluoro alkyl vinyl ether copolymer (PFA) or the like can be used.

It is noted that the phrase "not containing oxygen" means not containing oxygen as a constituent element and oxygen which adheres on a surface and oxygen inevitably contained are excluded.

The solder-repellant layer 22 is formed into a film by a coating method, a printing method, an ink-jet method, an evaporation method, a CVD method or a sputtering method, or the like. A pattern of the doughnut shape is formed by covering a central portion by a circular mask in advance and separating the mask after the film formation of the solder-repellant layer. In a screen printing method or the ink-jet method, the solder-repellant layer patterned without mask can be applied.

The solder-repellant layer 22 is necessary for preventing overflow of the solder but is unnecessary in view of optical performance of the optical unit 20. Therefore, the solder-repellant layer 22 is formed into the film in the doughnut shape to be limited to a range where the optical performance is not influenced.

It is preferable that thickness of the solder-repellant layer 22 is not less than 10 nm. In this range, a uniform film is easy formed and the layer has performance of preventing overflow of the solder. The thickness of the solder-repellant layer 22 does not have an upper limit in particular, but in view of productivity the upper limit is 100 μm, for example.

Besides, it is preferable that width W1 of the solder-repellant layer 22 (see FIG. 2) is not less than 0.005 mm, for example. In this range, it is possible to prevent the overflow of the solder. Further, it is more preferable that the width is not less than 0.03 mm for easily forming the solder-repellant layer precisely and continuously. It is preferable that an upper limit of the width of the solder-repellant layer 22 is set to be wider within a range in which the optical performance is not influenced.

Figure 3:
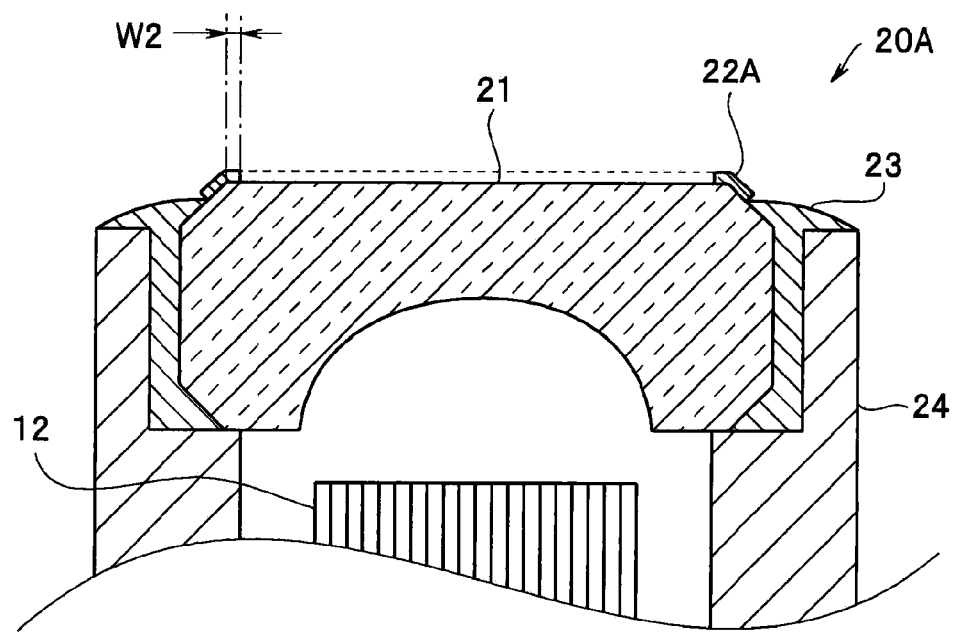
FIG. 3 is a sectional view of an irradiation optical unit of an endoscope according to the first embodiment.

Besides, as in an optical unit 20A shown in FIG. 3 in which a ridge line on which a distal end surface and the side surface of the lens 21 intersect is chamfered, the bonding member 23 composed of solder covers a chamfered surface as well as the side surface of the lens 21. Even in a case where the solder-repellant layer 22 cannot be formed to have a width not less than a predetermined width (W1) on the distal end surface of the lens 21 in view of optical characteristics of the optical unit 20, it is possible to prevent the melted solder from spreading on the distal end surface.

That is, as long as the melted solder can be prevented from spreading on the distal end surface of the lens to the range where the optical performance is influenced, the solder-repellant layer 22 may be formed into the film in the doughnut shape on at least one of the distal end surface and the chamfered surface of the lens 21.

The chamfering may be so-called corner-R machining which is cutting by a curved surface, as well as machining of cutting off the ridge line by a plane. Further, the chamfering includes a case of formation into the same shape as machined, and a method of machining or forming is not limited to a particular one.

For example, in a case of the lens 21 which is subjected to chamfering of "C0.05" and in which a range where the optical performance is influenced is defined by 0.05 mm inward from the chamfered portion, an outer circumference in a range of 0.05 mm on the distal end surface is a range in which the solder-repellant layer 22 can be formed, and the solder-repellant layer 22 can be formed on the distal end surface with a width (W2) of 0.05 mm as the maximum. Besides, "C0.05" means cutting off of an edge by an isosceles right triangle having sides in 0.05 mm long.

On the other hand, in the image pickup optical unit 30, a solder-repellant layer 32, which is composed of magnesium fluoride as a transparent material, is formed into a film on a substantially entire face of an outer surface of the lens 31. For example, the solder-repellant layer 32 is formed into the film in a region except an outer circumferential portion W3 (see FIG. 4) of the outer surface of the lens 31. W3 is set in a range where the optical performance is not influenced. For example, when the lens 31 has a diameter of 4 mm and an effective optical diameter of 3.8 mm, a value of W3 is 0.1 mm. It is noted that the lens 31 of the optical unit 30 is not chamfered, but may be chamfered.

As a material of the solder-repellant layer 32, a transparent material, such as aluminum nitride and magnesium fluoride, can be used from among the same materials for the solder-repellant layer 22. The bonding member 33 is made of the same solder as the bonding member 23.

It is preferable that thickness of the solder-repellant layer 32 is not less than 10 nm so as to securely prevent the melted solder from spreading on the outer surface. It is noted that the solder-repellant material such as aluminum nitride and magnesium fluoride is a transparent material but an optical interference effect occurs when a layer thickness increases. Therefore, it is preferable that the thickness of the solder-repellant layer 32 is not greater than 200 nm and it is particularly preferable that the thickness is not greater than 100 nm.

The endoscope 10 has high water-tight sealing properties between the lens 21 and the lens frame 24 and between the lens 31 and the lens frame 34, the lenses 21 and 31 being the optical members disposed at the distal end portion 11A and the lens frames 24 and 34 holding the lenses 21 and 31, respectively, and the endoscope 10 is easily manufactured.

Besides, in the endoscope 10 as described in the above embodiment, the solder-repellant layer is formed into the film in the doughnut shape on the outer circumferential portion of the outer surface of the lens 21 of the irradiation optical unit 20, and the solder-repellant layer is formed into the film on substantially the entirety of the outer surface of the lens 31 of the image pickup optical unit 30. By contrast, the solder-repellant layer may be formed into the film on the entire surface of the lens 21 or on the entire surfaces of both lenses 21 and 31, and may be formed into the film in the doughnut shape on the lens 31 or on both lenses 21 and 31.

Further, a first solder-repellant layer may be formed into the film on substantially the entirety of the outer surface of the lens, and further a second solder-repellant layer may be formed into the film in the doughnut shape on the outer circumferential portion.

Furthermore, in only one of the irradiation optical unit 20 and the image pickup optical unit 30, the lens with the solder-repellant layer formed into the film on the outer surface may be fixed to the lens frame without any member intervened.

Moreover, a plurality of irradiation optical units 20 or a plurality of image pickup optical units 30 may be disposed at the distal end portion 11A.

The lenses 21 and 31 are each a plano-concave lens having a negative power so that lens 21 irradiates the illumination light in a wide range and so that the lens 31 attains a wide field. However, the lenses 21 and 31 may be plano-convex lenses depending on the configuration of the optical units 20 and 30. However, it is preferable that the outer surfaces of the lenses 21 and 31 forming the outermost surfaces of the optical unit 20 and 30 are planes in order to prevent adherence and breakage by shock.

Besides, in a case of disposing a cover glass on the outermost surface side of the optical unit, a cover glass with a solder-repellant layer formed into a film may be bonded to the lens frame via the solder. That is, an optical member which is fixed to the lens frame in a water-tight sealing state may be a cover glass of a flat plate.

In the present embodiment, the solder is prevented from overflowing on the outer surface of the lens in soldering by forming the solder-repellant layer into the film on the outer surface of the lens. However, it may be configured that a cover jig made of the solder-repellant material may be pressed to cover the outer surface of the lens only when performing the soldering. Further, the solder-repellant layer formed into the film may be peeled after the soldering.

Besides, since the bonding member 23 is the low-temperature solder having a melting point not higher than 200° C. and forming a chemical bond via the oxygen, the lens frames 24 and 34 may be resin such as polysulfone or oxide ceramic such as almina. Further, since the bonding temperature is low, even if the lens is a glass which is weak in mechanical strength, an applied stress is small and therefore a crack or the like is hard to occur.

Second Embodiment

Next, an endoscope 10A according to the second embodiment will be described. Since the endoscope 10A is similar to the endoscope 10 of the first embodiment, the same reference sign is assigned to an element having the same function and the description thereof is omitted. Hereinafter, an example of an image pickup optical unit 30A will be described.

Figure 5:
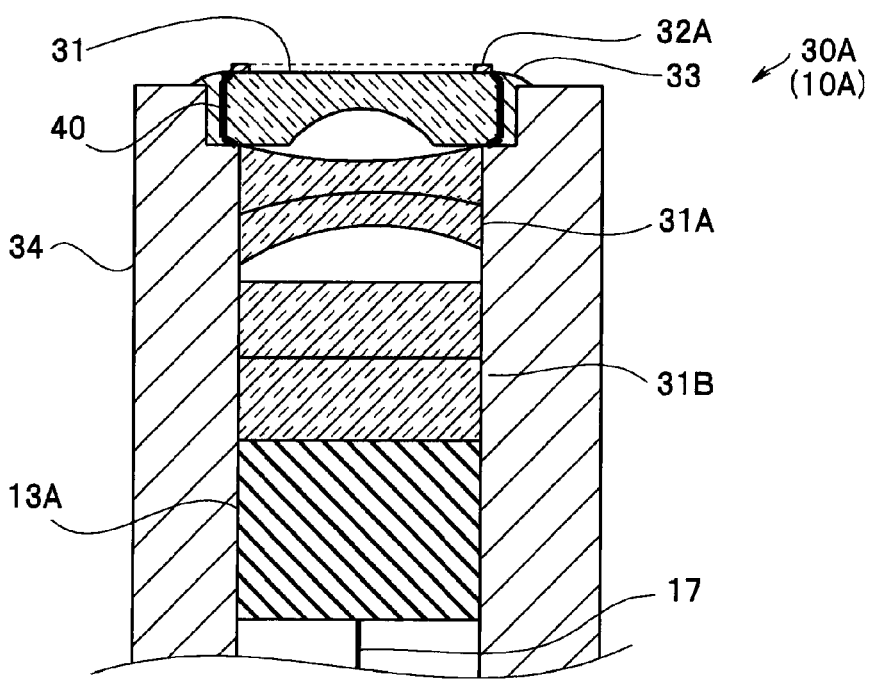
FIG. 5 is a sectional view of an image pickup optical unit of an endoscope according to a second embodiment.

The lenses of the optical units of the endoscope 10 of the first embodiment are fixed to the lens frames by solder without any other member intervened. By contrast, as shown in FIG. 5, in the image pickup optical unit 30A of the endoscope 10A, a black layer 40 containing carbon is applied on a side surface of the lens 31. That is, the lens 31 is fixed to the lens frame 34 by a bonding member 33 made of solder via the black layer 40.

The black layer 40 is effective in preventing a flare or a ghost in a picked-up image. In the endoscope 10, treatment is performed by projecting a treatment instrument from an opening at a distal end of the insertion portion inserted into a subject. The treatment instrument made of glossy metal such as stainless steel strongly reflects the illumination light. Since the reflected light enters the lens obliquely at a shallow angle in a horizontal direction of the lens and reflects or scatters on the side surface of the lens, the reflected or scattered light reaches the image pickup optical unit, and therefore the flare or the ghost is generated.

Particularly in a flexible endoscope, a light emitting lens of an illumination optical unit, a light incidence lens of an image pickup optical unit and an opening through which a treatment instrument is projected are located close to each other, and therefore the above phenomenon is prominent. Besides, in a rigid endoscope, since a treatment instrument is inserted into a body through a trocar separate from the endoscope, the above phenomenon is not as prominent as the flexible endoscope.

The black layer 40 containing carbon pigment or black organic dyestuff prevents light reflection on the side surface of the lens.

The carbon pigment is selected from carbon black, lamp black, furnace black, ivory black, graphite, fullerene, etc. On the other hand, as the black organic dyestuff, metal complex dye, cyan-based dye, azo-based dye, blackberry dye, chlorophyll dye, etc. can be used.

The pigment or the dyestuff is mixed with appropriate binder to produce paint and applied. As the binder, various thermoplastic resins and various thermosetting resins, e.g. epoxy resin, polyethylene, polypropylene, silicone resin and polyurethane, are used. It is easy to apply the black layer 40 even to the side surface.

Figure 4:
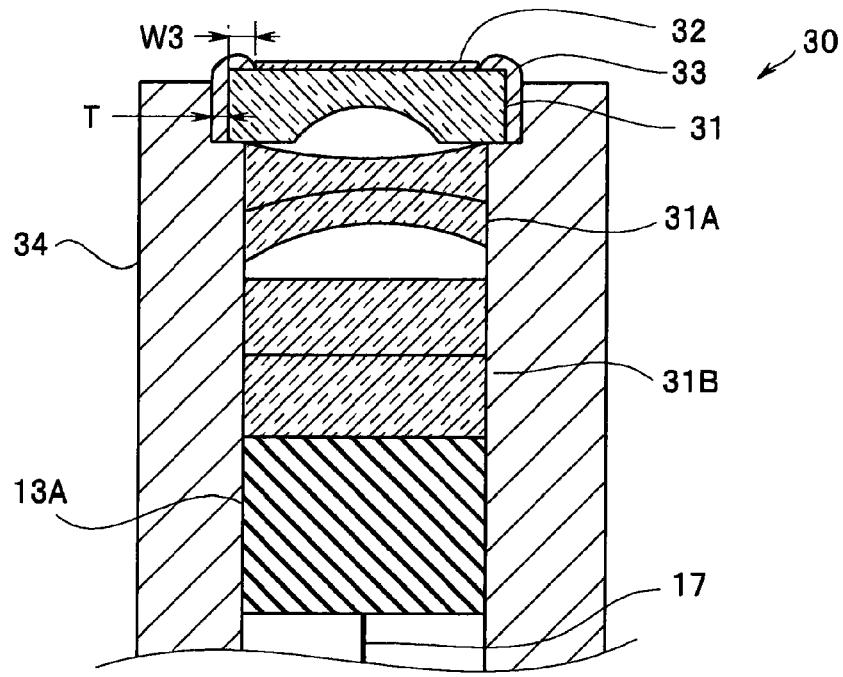
FIG. 4 is a sectional view of an image pickup optical unit of the endoscope according to the first embodiment.

Since the black layer 40 is thin in thickness, there is a little fear that moisture invades inside of the optical system through the black layer 40. Besides, it is preferable that the thickness of the black layer 40 is not greater than 1/10 of thickness T of the bonding member 33, and it is particularly preferable that the thickness is not greater than 5 μm, for example. Here, as shown in FIG. 4, the thickness T of the bonding member 33 is a gap between the lens and the lens frame. Besides, it is preferable that a lower limit of the thickness of the black layer 40 is not less than 0.01 μm so as to obtain a predetermined antireflection effect.

Further, in order to obtain a higher antireflection effect, it is preferable that the side surface of the lens 31 is a rough surface. The rough surface means a surface having an average surface roughness (Ra) not less than 0.1 μm and not greater than 1.5 μm.

Besides, if the lens is chamfered as shown in FIG. 5, it is preferable that the black layer 40 covers the chamfered surface as well as the side surface of the lens.

The solder of the bonding member 33 has the same composition as the solder described in the first embodiment and is the lead-free Sn-alloy solder containing at least one of Zn, Sb, Al and In that forms a chemical bond with a material including oxygen via the oxygen.

In general, the solder has low solder wettability with a material containing carbon. Therefore, it has been necessary to clean a solder bonding surface so that there is no organic matter on the surface. However, the solder of the bonding member 33 having the above composition has high solder wettability with the black layer containing carbon. Although a cause of this is not clear, it is considered that the solder forms a chemical bond via the carbon.

Further, since the bonding member 33 is the low-temperature solder having the melting point not higher than 200° C., the bonding member 33 does not damage the black layer 40.

As described above, the endoscope 10A of the present embodiment includes: an optical member having a solder-repellant layer applied on an outer circumferential portion of an outer surface in a doughnut shape, with a ridge line on which a distal end surface and a side surface of the optical member intersect being chamfered, the solder-repellant layer composed of magnesium fluoride, aluminum nitride, boron nitride, silicon nitride, silicon carbide, boron carbide, calcium carbide, diamond-like carbon, polytetrafluoroethylene or rafluoroethylene-perfluoro alkyl vinyl ether copolymer; a black layer containing carbon and applied on a side surface of the optical member; a frame portion that holds the optical member; and a bonding member that water-tightly fixes the optical member to the frame portion and covers the side surface and a chamfered surface of the optical member, the bonding member composed of lead-free Sn-alloy solder containing at least one of Zn, Sb, Al and In, having a melting point not higher than 200° C. and forming a chemical bond via oxygen, wherein the optical member, the black layer, the frame portion and the bonding member are provided at a distal end portion of an insertion portion.

Besides, in at least one of the irradiation optical unit and the image pickup optical unit, the lens with the solder-repellant layer applied on the outer surface may be fixed to the lens frame via the black layer 40.

The endoscope 10A has the effects of the endoscope 10 and further has a little adverse influence by internal reflection.

The present invention is not limited to the above-described embodiments, etc. and may be subjected to various changes, combinations, modifications and the like.

What is claimed is:

1. An endoscope comprising, at a distal end portion of an insertion portion:
    an optical member with a ridge line on which a distal end surface and a side surface of the optical member intersect being chamfered;
    a black layer containing carbon and applied on the side surface of the optical member;
    a frame portion that holds the optical member, the frame portion being made of metal; and
    a bonding member that water-tightly fixes the optical member to the frame portion and covers the side surface of the optical member and a chamfered surface of the optical member, the bonding member being composed of a lead-free Sn-alloy solder having a melting point not higher than 200° C.,
    wherein the lead-free Sn-alloy solder forms a chemical bond via oxygen, and wherein a solder-repellant layer composed of magnesium fluoride, aluminum nitride, boron nitride, silicon nitride, silicon carbide, boron carbide, calcium carbide, diamond-like carbon, polytetrafluoroethylene or tetrafluoroethylene-perfluoro alkyl vinyl ether copolymer is applied on an outer circumferential portion of an outer surface of the optical member in a doughnut shape.

2. The endoscope according to claim 1, wherein the optical member is made of quartz, sapphire, stabilized zirconia, yttrium aluminum garnet, or amorphous glass.

3. An endoscope comprising, at a distal end portion of an insertion portion:
    an optical member;
    a frame portion that holds the optical member, the frame portion being made of metal; and
    a bonding member that water-tightly fixes the optical member to the frame portion, the bonding member being composed of an Sn-alloy solder containing at least one of Zn, Sb, Al and In and having a melting point not higher than 200° C.,
    wherein the Sn-alloy solder forms a chemical bond via oxygen, and wherein
    a solder-repellant layer composed of metal carbide, metal nitride, metal boride, metal fluoride, fluororesin or carbon material is applied on an outer circumferential portion of an outer surface of the optical member in a doughnut shape.

4. The endoscope according to claim 3, wherein the solder-repellant layer is composed of magnesium fluoride, aluminum nitride, boron nitride, silicon nitride, silicon carbide, boron carbide, calcium carbide, diamond-like carbon, polytetrafluoroethylene or tetrafluoroethylene-perfluoro alkyl vinyl ether copolymer.

5. The endoscope according to claim 4, wherein a ridge line on which a distal end surface of the optical member and a side surface of the optical member intersect is chamfered and the bonding member covers the side surface of the optical member and a chamfered surface of the optical member.

6. The endoscope according to claim 5, further comprising a black layer containing carbon and applied on the side surface of the optical member.

7. The endoscope according to claim 6, wherein a thickness of the black layer is not greater than 1/10 of a thickness of the bonding member.

8. The endoscope according to claim 5, wherein the optical member is fixed to the frame portion by the bonding member without any other member intervened.

9. The endoscope according to claim 3, wherein the optical member is made of quartz, sapphire, stabilized zirconia, yttrium aluminum garnet, or amorphous glass.

* * * * *